US007303646B2

(12) United States Patent
Qvist

(10) Patent No.: US 7,303,646 B2
(45) **Date of Patent: *Dec. 4, 2007**

(54) METHOD AND KIT PROVIDING BIOADHESIVE BINDING OR COATING WITH POLYPHENOLIC MUSSEL PROTEINS

(75) Inventor: Magnus Qvist, Alingsås (SE)

(73) Assignee: Biopolymer Products of Sweden AB, Alingsas (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/498,793

(22) PCT Filed: Dec. 13, 2002

(86) PCT No.: PCT/SE02/02321

§ 371 (c)(1), (2), (4) Date: Jun. 14, 2004

(87) PCT Pub. No.: WO03/051418

PCT Pub. Date: Jun. 26, 2003

(65) Prior Publication Data

US 2005/0016676 A1 Jan. 27, 2005

Related U.S. Application Data

(60) Provisional application No. 60/354,478, filed on Feb. 8, 2002.

(30) Foreign Application Priority Data

Dec. 14, 2001 (SE) .................................... 0104227

(51) Int. Cl.
*B32B 31/26* (2006.01)
*C07K 14/00* (2006.01)

(52) U.S. Cl. .................................... 156/307.1; 530/350

(58) Field of Classification Search ................ 530/350; 156/307.1; 435/68.1
See application file for complete search history.

(56) References Cited

U.S. PATENT DOCUMENTS 5,242,808 A 9/1993 Maugh et al.
5,410,023 A 4/1995 Burzio
5,817,470 A 10/1998 Burzio et al.
6,506,577 B1 1/2003 Deming et al.

FOREIGN PATENT DOCUMENTS

WO 01/44401 A1 6/2001

OTHER PUBLICATIONS

Miaoer Yu and Timothy J. Deming, Synthetic Polypeptide Mimics of Marine Adhesives, Macromolecules, vol. 31(15), pp. 4739-4745, 1998.*

Rzepecki et al; "DOPA Proteins: Versatile Varnishes and Adhesives From Marine Fauna"; College of Marine Studies, University of Delaware, Lewes, DE, 1998, pp. 118-148.

Saby et al.; "Mytilus Edulis Adhesive Protein (MAP) as an Enzyme Immobilization Matrix in the Fabrication of Enzyme-Based Electrodes"; Electroanalysis, 1998, vol. 10, No. 17, pp. 1193-1199.

Fischer et al., Biomaterials 24 (2003) 1121-1131.

Morgan et al., Journal of cell Science 94 (1989) 553-559.

Abstract of King et al., 3 Biomed Matr Res A 2003, 64, 533-9.

Abstract of Strand et al., Cell Transplant 2001, 10, 263-75.

Abstract Needham et al., Lab Invest 1988 538-548.

* cited by examiner

*Primary Examiner*—Robert B. Mondesi
(74) *Attorney, Agent, or Firm*—Nixon & Vanderhye P.C.

(57) ABSTRACT

The present invention pertains to a method for attaching two surfaces to each other or coating a surface, comprising the steps of providing a bioadhesive composition consisting of a bioadhesive polyphenolic protein derived from a byssus-forming mussel, mixing the bioadhesive protein with a strongly alkaline solution before or simultaneously as applying the composition to the surfaces which are to be attached to each other or the surface to be coated. The surfaces are then joined and left for a sufficiently long time to allow curing to occur alternatively the surface coated by the composition is left for a sufficiently long time to allow curing to occur. The invention can be provided as a kit of parts comprising the bioadhesive protein solution and a preparation of a strongly alkaline solution.

16 Claims, No Drawings

SEQUENCE LISTING

```
<160> NUMBER OF SEQ ID NOS: 11

<210> SEQ ID NO 1
<211> LENGTH: 9
<212> TYPE: PRT
<213> ORGANISM: Mytilus edulis
<220> FEATURE:
<221> NAME/KEY: X
<222> LOCATION: (4)..(6)
<223> OTHER INFORMATION: X is DOPA

<400> SEQUENCE: 1

Val Gly Gly Xaa Gly Xaa Gly Ala Lys
1               5


<210> SEQ ID NO 2
<211> LENGTH: 10
<212> TYPE: PRT
<213> ORGANISM: Mytilus edulis
<220> FEATURE:
<221> NAME/KEY: X
<222> LOCATION: (6)..(6)
<223> OTHER INFORMATION: X is dihydroxy proline
<220> FEATURE:
<221> NAME/KEY: X
<222> LOCATION: (7)..(7)
<223> OTHER INFORMATION: X is hydroxy proline
<220> FEATURE:
<221> NAME/KEY: X
<222> LOCATION: (9)..(9)
<223> OTHER INFORMATION: X is DOPA

<400> SEQUENCE: 2

Ala Lys Pro Ser Tyr Xaa Xaa Thr Xaa Lys
1               5                   10


<210> SEQ ID NO 3
<211> LENGTH: 8
<212> TYPE: PRT
```

-continued

```
<213> ORGANISM: Mytilus edulis
<220> FEATURE:
<221> NAME/KEY: X
<222> LOCATION: (3)..(7)
<223> OTHER INFORMATION: X is DOPA

<400> SEQUENCE: 3

Thr Gly Xaa Gly Pro Gly Xaa Lys
1               5


<210> SEQ ID NO 4
<211> LENGTH: 7
<212> TYPE: PRT
<213> ORGANISM: Mytilus edulis
<220> FEATURE:
<221> NAME/KEY: X
<222> LOCATION: (1)..(7)
<223> OTHER INFORMATION: X is DOPA

<400> SEQUENCE: 4

Ala Gly Xaa Gly Gly Leu Lys
1               5


<210> SEQ ID NO 5
<211> LENGTH: 11
<212> TYPE: PRT
<213> ORGANISM: Mytilus edulis
<220> FEATURE:
<221> NAME/KEY: X
<222> LOCATION: (1)..(11)
<223> OTHER INFORMATION: X is DOPA

<400> SEQUENCE: 5

Gly Pro Xaa Val Pro Asp Gly Pro Tyr Asp Lys
1               5                   10


<210> SEQ ID NO 6
<211> LENGTH: 11
<212> TYPE: PRT
<213> ORGANISM: Mytilus edulis
<220> FEATURE:
<221> NAME/KEY: X
<222> LOCATION: (1)..(11)
<223> OTHER INFORMATION: X is DOPA

<400> SEQUENCE: 6

Gly Lys Pro Ser Pro Xaa Asp Pro Gly Xaa Lys
1               5                   10


<210> SEQ ID NO 7
<211> LENGTH: 3
<212> TYPE: PRT
<213> ORGANISM: Mytilus edulis
<220> FEATURE:
<221> NAME/KEY: X
<222> LOCATION: (1)..(3)
<223> OTHER INFORMATION: X is DOPA

<400> SEQUENCE: 7

Gly Xaa Lys
1


<210> SEQ ID NO 8
<211> LENGTH: 8
<212> TYPE: PRT
<213> ORGANISM: Mytilus edulis
<220> FEATURE:
<221> NAME/KEY: X
<222> LOCATION: (1)..(8)
```

-continued

```
<223> OTHER INFORMATION: X is DOPA

<400> SEQUENCE: 8

Thr Gly Xaa Ser Ala Gly Xaa Lys
1               5


<210> SEQ ID NO 9
<211> LENGTH: 9
<212> TYPE: PRT
<213> ORGANISM: Mytilus edulis
<220> FEATURE:
<221> NAME/KEY: X
<222> LOCATION: (1)..(9)
<223> OTHER INFORMATION: X is DOPA

<400> SEQUENCE: 9

Gln Thr Gly Xaa Val Pro Gly Xaa Lys
1               5


<210> SEQ ID NO 10
<211> LENGTH: 9
<212> TYPE: PRT
<213> ORGANISM: Mytilus edulis
<220> FEATURE:
<221> NAME/KEY: X
<222> LOCATION: (1)..(9)
<223> OTHER INFORMATION: X is DOPA

<400> SEQUENCE: 10

Gln Thr Gly Xaa Asp Pro Gly Tyr Lys
1               5


<210> SEQ ID NO 11
<211> LENGTH: 9
<212> TYPE: PRT
<213> ORGANISM: Mytilus edulis
<220> FEATURE:
<221> NAME/KEY: X
<222> LOCATION: (1)..(9)
<223> OTHER INFORMATION: X is DOPA

<400> SEQUENCE: 11

Gln Thr Gly Xaa Leu Pro Gly Xaa Lys
1               5
```

METHOD AND KIT PROVIDING BIOADHESIVE BINDING OR COATING WITH POLYPHENOLIC MUSSEL PROTEINS

This application is the US national phase of international application PCT/SE02102321 filed 13 Dec. 2002, which designated the US. PCT/SE02/0232 claims priority to SE Application No. 0104227-4 filed 14 Dec. 2001 and U.S. application Ser. No. 60/354,478 filed 08 Feb. 2002. The entire contents of these applications are incorporated herein by reference.

The present invention pertains to a method for attaching two surfaces to each other or coating a surface, comprising the steps of providing a bioadhesive composition consisting of a bioadhesive polyphenolic protein derived from a byssus-forming mussel, mixing the bioadhesive protein with a strongly alkaline solution before or simultaneously as applying the composition to the surfaces which are to be attached to each other or the surface to be coated. The surfaces are then joined and left for a sufficiently long time to allow curing to occur alternatively the surface coated by the composition is left for a sufficiently long time to allow curing to occur. The invention can be provided as a kit of parts comprising the bioadhesive protein solution and a preparation of a strongly alkaline solution.

BACKGROUND OF THE INVENTION

Attachment of different structures is crucial in a wide variety of processes. However, this is frequently associated with problems of different nature depending on what structures are to be attached.

Areas that are particulary troublesome are adhesion in the medical field, and attachment of components of very small size, such as in the micro- and nano-techniques. In the medical field, examples of when adhesives have to be used to adhere biological material include repair of lacerated or otherwise damaged organs, especially broken bones and detached retinas and corneas. Dental procedures also often require adhesion of parts to each other, such as during repair of caries, permanent sealants and periodontal surgery. It is very important in bio-medical applications of an adhesive and coating composition to use bioacceptable and biodegradable components, which furthermore should not per se or due to contamination induce any inflammation or toxic reactions. In addition, the adhesive has to be able to attach structures to each other in a wet environment. In the electronic industry, a particular problem today is that the components that are to be attached to each other often are of very small size, and the amount of adhesive that is possible to use is very small. Adhesives that provide high adhesive strength even with minor amounts of adhesive are therefore required. Also for non-medical uses, an adhesive that is non-irritating, non-allergenic, non-toxic and environmentally friendly is preferred, in contrast to what many of the adhesives commonly used today usually are.

Polyphenolic proteins, preferentially isolated from mussels, are known to act as adhesives. Examples of such proteins can be found in e.g. U.S. Pat. No. 4,585,585. Their wide use as adhesives has been hampered by problems related to the purification and characterisation of the adhesive proteins in sufficient amounts. Also, mostly when using the polyphenolic proteins as adhesives the pH has had to be raised to neutral or slightly basic (commonly to from 5.5 to 7.5) in order to facilitate oxidation and curing of the protein. However, this curing is slow and results in poor adhesive strength and therefore oxidisers, fillers and cross-linking agents are commonly added to decrease the curing time and obtain a stronger adhesive.

Mussel adhesive protein (MAP) is formed in a gland in the foot of byssus-forming mussels, such as the common blue mussel (*Mytilus edulis*). The molecular weight of MAP from *Mytilus edulis* is about 130.000 Dalton and it has been disclosed to consist of 75-80 closely related repeated peptide sequences. The protein is further characterised by its many epidermal growth factor like repeats. It has an unusual high proportion of hydroxy-containing amino acids such as hydroxyproline, serine, threonine, tyrosin, and the uncommon amino acid 3,4-dihydroxy-L-phenylalanine (Dopa) as well as lysine. It may be isolated either from natural sources or produced biotechnologically. U.S. Pat. No. 5,015,677 as well as U.S. Pat. No. 4,585,585 disclose that MAP has very strong adhesive properties after oxidation and polymerisation, e.g. by the activity of the enzyme tyrosinase, or after treatment with bifunctional reagents.

MAP is previously known to be useful as an adhesive composition e.g. for ophthalmic purposes. Robin et al., Refractive and Corneal Surgery, vol. 5, p. 302-306, and Robin et al., Arch. Ophthalmol., vol. 106, p. 973-977, both disclose MAP-based adhesives comprising an enzyme polymiser. U.S. Pat. No. 5,015,677 also describes a MAP-based adhesive containing a cross-linking agent and optionally a filler substance and a surfactant. Preferred cross-linking agents according to U.S. Pat. No. 5,015,677 are enzymatic oxidising agents, such as catechol oxidase and tyrosinase, but sometimes also chemical cross-linking agents, such as glutaraldehyde and formaldehyde can be used. Examples of fillers are proteins, such as casein, collagen and albumin, and polymers comprising carbohydrate moieties, such as chitosan and hyaluronan. U.S. Pat. No. 5,030,230 also relates to a bioadhesive comprising MAP, mushroom tyrosinase (cross-linker), SDS (sodium dodecyl sulfate, a surfactant) and collagen (filler). The bioadhesive is used to adhere a cornea prosthesis to the eye wall.

EP-A-343 424 describes the use of a mussel adhesive protein to adhere a tissue, cell or another nucleic acid containing sample to a substrate during nucleic acid hybridisation conditions, wherein the mussel adhesive protein, despite the harsh conditions encountered during the hybridisation, provided adherence. U.S. Pat. No. 5,817,470 describes the use of mussel adhesive protein to immobilise a ligand to a solid support for enzyme-linked immunoassay. Mussel adhesive protein has also been used in cosmetic compositions to enhance adherence to nails and skin (WO 88/05654).

A major problem associated with known MAP-based bioadhesive compositions, despite the superior properties of MAP per se, is that some constituents, in particular the presently used cross-linking agents, can harm and/or irritate living tissue and cause toxic and immunological reactions. Chemical crosslinking agents, such as glutaraldehyde and formaldehyde, are generally toxic to humans and animals, and it is highly inappropriate to add such agents to a sensitive tissue, such as the eye. Enzymes, such as catechol oxidase and tyrosinase, are proteins, and proteins are generally recognised as potential allergens, especially in case they originate from a species other than the patient. Because of their oxidising and hydrolysing abilities, they can also harm sensitive tissue.

Therefore, there is still a need for new adhesive compositions, both for medical and other applications, that provide strong adhesion with small amounts of adhesive, that are simple to use and that do not cause toxic and allergic reactions.

SUMMARY OF THE INVENTION

The present invention pertains to a method for attaching two surfaces to each other or coating a surface, comprising the steps of providing a bioadhesive composition consisting of a bioadhesive polyphenolic protein derived from a byssus-forming mussel, mixing the bioadhesive protein with a strongly alkaline solution before applying the composition to the surfaces which are to be attached to each other or the surface to be coated. The surfaces are then joined and left for a sufficiently long time to allow curing to occur or the surface coated is left to cure for a sufficiently long time. The invention can be provided as a kit of parts comprising the bioadhesive protein solution and a preparation of a strongly alkaline solution. Since the provided compositions are non-toxic and presumably non-allergenic the invention is especially suitable for use in medical applications for adherence or coating in biological tissues. Also, since very strong adhesive strengths are provided using the compositions of the present invention, it is also particularly useful for applications where only minute amounts of adhesives can be used, including non-biological surfaces.

Definitions

As disclosed herein, the terms “polyphenolic protein”, “mussel adhesive protein” or “MAP” relates to a bioadhesive protein derived from byssus-forming mussels. Examples of such mussels are mussels of the genera *Mytilus, Geukensia, Aulacomya, Phragmatopoma, Dreissenia* and *Brachiodontes*. Suitable proteins have been disclosed in a plurality of publications, e.g. U.S. Pat. Nos. 5,015,677, 5,242,808, 4,585,585, 5,202,236, 5,149,657, 5,410,023, WO 97/34016, and U.S. Pat. No. 5,574,134, Vreeland et al., J. Physiol., 34: 1-8, and Yu et al., Macromolecules, 31: 4739-4745. They comprise about 30-300 amino acid residues and essentially consist of tandemly linked peptide units optionally separated by a junction sequence of 0-10 amino acids. A characteristic feature of such proteins is a comparatively high amount of positively charged lysine residues, and in particular the unusual amino acid DOPA (L-3,4-dihydroxyphenylalanine). A polyphenolic protein suitable for use in the present invention has an amino acid sequence in which at least 3% and preferably 6-30% of the amino acid residues are DOPA. A few examples of typical peptide units are given below. However, it is important to note that the amino acid sequences of these proteins are variable and that the scope of the present invention is not limited to the exemplified subsequences below as the skilled person realises that bioadhesive polyphenolic proteins from different sources can be regarded as equivalent:

a) Val-Gly-Gly-DOPA-Gly-DOPA-Gly-Ala-Lys (SEQ ID NO:1)
b) Ala-Lys-Pro-Ser-Tyr-diHyp-Hyp-Thr-DOPA-Lys (SEQ ID NO:2)
c) Thr-Gly-DOPA-Gly-Pro-Gly-DOPA-Lys (SEQ ID NO:3)
d) Ala-GIy-DOPA-Gly-Gly-Leu-Lys (SEQ ID NO:4)
e) Gly-Pro-DOPA-Val-Pro-Asp-Gly-Pro-Tyr-Asp-Lys (SEQ ID NO:5)
f) Gly-Lys-Pro-Ser-Pro-DOPA-Asp-Pro-Gly-DOPA-Lys (SEQ ID NO:6)
g) Gly-DOPA-Lys (SEQ ID NO:7)
h) Thr-Gly-DOPA-Ser-Ala-Gly-DOPA-Lys (SEQ ID NO:8)
i) Gln-Thr-Gly-DOPA-Val-Pro-Gly-DOPA-Lys (SEQ ID NO:9)
j) Gln-Thr-Gly-DOPA-Asp-Pro-Gly-Tyr-Lys (SEQ ID NO:10)
k) Gln-Thr-Gly-DOPA-Leu-Pro-Gly-DOPA-Lys (SEQ ID NO:11)

The term “surface” is to be interpreted broadly and may comprise virtually any surface. The choice of surface is not critical to the present invention. Examples of surfaces for which the invention are specially suitable for include non-biological surfaces such as glass, plastic, ceramic and metallic surfaces etc., and biological surfaces, comprising wood and different tissues such as skin, bone, teeth, the eye, cartilage, etc.

By “sufficiently long time” is meant a time period long enough to allow curing of the bioadhesive composition. Typically the time period required is from at least 10 sec to one hour.

By “strongly alkaline solution” is meant an aqueous alkaline solution, the pH of said strongly alkaline solution being 10 or more, preferably 11 or more.

DETAILED DESCRIPTION OF THE INVENTION

The object of the present invention is to provide an adhesive composition to be used for attaching two surfaces to each other or coating a surface. The compositions provided in the invention can in principle be used to attach any surfaces to each other or to coat any surface. However, the compositions according to the present invention are particularly useful when adhesive or coating compositions are needed that are non-toxic, non-irritating or non-allergenic, or that can be used in wet environments. Also the compositions of the present invention are useful when a strong adhesion even with small amounts of adhesive, are required. Further advantages with the compositions provided in the present invention are their water solubility, the avoidance of organic solvents commonly used in adhesive or coating compositions, that they are biologically produced and harmless to the environment.

The only mandatory components of the present invention is the polyphenolic protein and an alkaline solution. Previously when polyphenolic proteins have been used, it has been thought to be necessary to add additional components, such as fillers and oxidising agents, in order to achieve strong enough adhesive strength and the pH is commonly raised to neutral or slightly basic. The present inventor has shown that a very strong adhesion, comparable to the adhesive strength provided using the commonly used MAP compositions, can be provided simply using a solution of the MAP protein and raising the pH when using the composition, employing a very strongly alkaline solution with a pH of 10 or more, preferably of 11 or more. Preferred bases for the present invention are bases such as NaOH, KOH, $NH_3$ and $Na_2CO_3$.

Preferably, the MAP concentration of the present invention is above 10 mg/ml. More preferably the concentration of the MAP-solution is above 20 mg/ml. Typically the concentration is between 20 and 50 mg/ml.

One preferred object of the present invention is to provide an adhesive or coating composition for medical applications, e.g. for attaching biological and/or non-biological components to biological structures, an object for which the MAP protein in itself is well suited, since it is non-toxic and biodegradable. However, the components commonly added to MAP compositions in order to obtain cross-linking and oxidation (chemical and/or enzymatic crosslinkers and oxidising agents) of the composition can lead to irritation and allergic reactions and those MAP compositions are therefore not optimal for medical applications. Due to the lack of such components in the present invention, the compositions of the present invention are particularly suitable for attachment of biological surfaces to each other or to biological or non-biological components. For the above reasons the compositions of the present invention are also particularly useful for coating of materials used in medical applications or biological tissues.

Due to the very high adhesive strength provided with very small amounts of the compositions of the present invention, one preferred field of application for which the compositions are particularly suitable for attachment of non-biological surfaces such as glass, plastic, ceramic and metallic surfaces. This is particularly useful within the electronic micro- and nano-techniques, optics, etc. for adhesion or coating of, for example, biosensors, microchips, solar cells, mobile phones, etc., since for these applications only minute amounts of adhesive can be used. The compositions of the present invention are also suitable for coating of non-biological surfaces.

The adhesive compositions of the present invention are also useful for attachment of cells, enzymes, antibodies and other biological specimen to surfaces.

According to one aspect of the invention the solution of MAP is mixed with a strongly alkaline solution with a pH of 10 or more, preferably 11 or more. The mixture is then applied to at least one of the surfaces to be attached to each other or to the surface to be coated. Alternatively, the MAP-solution and the strongly alkaline solution are separately applied, without any specific order, to at least one of the surfaces, which are to be attached to each other, or a surface to be coated. The MAP-solution can also be applied to one of the surfaces that are to be attached to each other while the strongly alkaline solution is applied to the other. If two surfaces are to be attached to each other they are then joined. Finally the attached or coated surfaces are left for a sufficiently long time to allow curing. The time necessary for curing will for example depend on the surfaces attached or coated, and the amount and the composition of the adhesive.

The present invention is preferably provided as a kit of parts useful in a method for attaching surfaces to each other or coating surfaces, comprising the MAP-solution, a preparation of the strongly alkaline solution and optionally at least one device, such as a syringe, to apply the compositions to the surfaces that are to be attached or coated. Preferred pH, concentration ranges of the MAP-solution, curing times and surfaces for use of this kit are as described above.

EXAMPLE 1

Determination of Adhesive Strength for Adhesion between Glass and Biological Tissue with Under Wet Conditions In order to determine the adhesive strength using the compositions of the present invention, the adhesive strength between glass plates and biological tissue (muscle from cattle and pig) was determined. The MAP-solution (in 0.01 M citric acid, from Biopolymer Products of Sweden AB. Alingsås, Sweden) of varying concentration and volumes (see Table 1 and 2) was applied to a glass plate (75×25×2 mm). Thereafter the strongly alkaline solution (NaOH, see Table 1 and 2) was applied and carefully mixed with the MAP-solution on the glass plate before the biological tissue (approximately of the size 40×15×4 mm) was placed on the glass plate and fixed with a clip. The pH of the NaOH solutions employed were: 1M NaOH pH 14 and 0.1 M NaOH pH 12.5. The samples were allowed to cure under water (35° C. for 10 min [Table 1], or 1 hour [Table 2]). The adhered surface between the glass plate and the biological tissue was in most cases 0.2-0.4 $cm^2$, with a variation from 0.1 to 0.8.

To measure the adhesive strength, the clip was removed from the sample and the sample was attached to a spring balance via the glass plate. The biological tissue was then pulled until it detached from the glass plate and the force needed for this was determined (Table 1 and 2).

Control samples were prepared as described above but instead of an alkaline solution an oxidant ($NaIO_4$, see Table 1 and 2) was mixed with the MAP-solution before joining the two surfaces.

As can be seen from Table 1 and 2, the adhesive strength employing the compositions of the present invention (MAP together with a strongly alkaline solution), adhesive strengths similar or above what could be achieved using an oxidant were unexpectedly obtained.

EXAMPLE 2

Determination of Adhesive Strength for Adhesion between Biological Tissues with Curing Under Wet Conditions In order to determine the adhesive strength using the compositions of the present invention, the adhesive strength between two attached biological tissues (muscle from cattle and pig) was determined. The MAP-solution (in 0.01 M citric acid, from Biopolymer Products of Sweden AB, Alingsås, Sweden) of varying concentration and volumes (see Table 3) was applied to one of the surfaces that were to be attached to each other. Thereafter the strongly alkaline solution (NaOH, see Table 3) was applied and carefully mixed with the MAP-solution before joining the two surfaces and fixing them with a clip. The pH of the NaOH solution employed was 12.5. The sample was thereafter placed under water (35° C. for one hour) for curing to occur. The adherence surfaces were in most cases 0.2-0.4 $cm^2$, with a variation from 0.1 to 0.8.

TABLE 1

Adhesive strength between glass plates and biological tissue with curing at 35° C. under water for 10 min.

| Sample | MAP Concentration (mg/ml) | MAP Amount (μg) | NaOH Concentration (M) | NaOH Amount (μl) | $NaIO_4$ Concentration (M) | $NaIO_4$ Amount (μl) | Adhesive strength (g) |
|---|---|---|---|---|---|---|---|
| 1 | 28 | 84 | 1.0 | 2 | — | — | 130 |
| 2 | 27 | 81 | 1.0 | 2 | — | — | 110 |
| 3 | 28 | 84 | — | — | 0.01 | 2 | 70 |

TABLE 2

Adhesive strength between glass plates and biological tissue with curing at 35° C. under water for 1 hour.

| Sample | MAP Concentration (mg/ml) | MAP Amount (μg) | NaOH Concentration (M) | NaOH Amount (μl) | $NaIO_4$ Concentration (M) | $NaIO_4$ Amount (μl) | Adhesive strength (g) |
|---|---|---|---|---|---|---|---|
| 1 | 23 | 69 | 1.0 | 2 | — | — | 100 |
| 2 | 23 | 69 | 1.0 | 2 | — | — | 150 |
| 3 | 25 | 75 | 1.0 | 2 | — | — | 100 |
| 4 | 23 | 69 | 0.1 | 2 | — | — | 120 |
| 5 | 23 | 69 | — | — | 0.01 | 2 | 110 |

TABLE 3

Adhesive strength between biological tissues with curing at 35° C. under water for 1 hour.

| Sample | MAP Concentration (mg/ml) | MAP Amount (μg) | NaOH Concentration (M) | NaOH Amount (μl) | $NaIO_4$ Concentration (M) | $NaIO_4$ Amount (μl) | Adhesive strength (g) |
|---|---|---|---|---|---|---|---|
| 1 | 18 | 54 | 0.1 | 1.5 | — | — | 190 |
| 2 | 18 | 54 | — | — | 0.01 | 1.5 | 150 |

To measure the adhesive strength, the clip was removed from the sample and one of the two attached surfaces was attached to a spring balance. The other surface was then pulled until detachment occurred and the force needed for this was determined (see Table 3).

Control samples were prepared as described above but instead of an alkaline solution an oxidant ($NaIO_4$, see Table 3) was mixed with the MAP-solution before joining the two surfaces.

As can be seen from Table 3, the adhesive strength employing the compositions of the present invention (MAP together with a strongly alkaline solution), adhesive strength above what could be achieved using an oxidant was unexpectedly obtained.

The biological tissues has an inherent property for adherence to each other. The values given in Table 3 are colTected for this effect.

EXAMPLE 3

Determination of Adhesive Strength for Adhesion between Glass and Biological Tissue with Curing Under Dry Conditions In order to determine the adhesive strength using the compositions of the present invention with curing under dry conditions for short time periods, the adhesive strength between attached glass plates and biological tissue (muscle from cattle and pig) was determined. The MAP-solution (in 0.01 M citric acid, from Bio-polymer Products of Sweden AB, Alingsås, Sweden) (see Table 4) was applied to a glass plate (75×25×2 mm) before the strongly alkaline solution of varying concentrations (NaOH, see Table 4) was applied and carefully mixed with the MAP-solution on the glass plate. The pH of the NaOH solutions employed were: 1M NaOH pH 14 and 0.1 M pH 12.5. Thereafter, the biological tissue (approximately of the size 40×15×4 mm) was placed on the glass plate and fixed with a clip. The sample was allowed to cure for 1 min at room temperature. The adhered surface between the glass plate and the biological tissue was in most cases 0.3-0.4 $cm^2$.

To measure the adhesive strength, the clip was removed from the sample and the sample was attached to a spring balance via the glass plate. The biological tissue was then pulled until it detached from the glass plate and the force needed for this was determined (see Table 4).

The adhesive strength employing $Na_2CO_3$ as a strongly alkaline base were also performed in an identical way as described above (Table 4). The pH of the 1M $Na_2CO_3$ was 11.5.

EXAMPLE 4

Determination of Adhesive Strength for Adhesion between Non-biological Materials In order to determine the adhesive properties of the compositions of the present invention when used for attachment of non-biological materials, the adhesive strength obtained between two glass plates was determined. The MAP-solution (in 0.01 M citric acid, from Biopolymer Products of Sweden AB, Alingsås, Sweden) (see Table 5) was applied to a glass plate (75×25×2 mm) before the strongly alkaline solution (1.0 M NaOH, pH 14) was applied and carefully mixed with the MAP-solution on the glass plate. Thereafter a second glass plate was placed onto the first glass plate with the adhesive composition and fixed with a clip. The overlapping surface between the glass plates was ca 2.5 to 3.0 $cm^2$, and the adhered surface was 0.4-0.5 $cm^2$. The glass plates were left to cure at room temperature for 72 hours, before determination of shear strength. The grip length was 75 mm and the cross head speed was 3 mm/min during determination of shear strength. For comparison the adhesive strength between glass plates employing common epoxy adhesive (Bostic AB, Helsingborg, Sweden) (10 mg) was determined. The epoxy adhesive covered a surface of 0.7-0.8 $cm^2$.

The adhesive strength obtained using the compositions the present invention resulted in very strong adhesive strengths, that can be compared to the adhesive strengths obtained employing ca 250 times more of a common epoxy glue (see Table 5). Therefore very high adhesive strengths can be obtained with very small amounts of adhesive when using the compositions of the present invention.

TABLE 4

Adhesive strength between glass plates and biological tissue with curing in dry environment at room temperature for 1 min.

| Sample | MAP Concentration (mg/ml) | MAP Amount (μg) | NaOH or $Na_2CO_3$ (only sample 6) Concentration (M) | NaOH or $Na_2CO_3$ (only sample 6) Amount (μl) | Adhesive strength (g) |
|---|---|---|---|---|---|
| 1 | 24 | 60 | 3 | 3 | 50 |
| 2 | 24 | 60 | 3 | 3 | 50 |
| 3 | 24 | 60 | 1 | 3 | 40 |
| 4 | 24 | 60 | 1 | 3 | 60 |
| 5 | 24 | 60 | 0.1 | 3 | 25 |
| 6 | 24 | 48 | 1.0 | 3 | 100 |

TABLE 5

Adhesive strength between non-biological materials with curing in a dry environment at room temperature for 72 hours.

| Sample | MAP Concentration (mg/ml) | MAP Amount (μg) | NaOH Concentration (M) | NaOH Amount (μl) | Epxoy glue Amount (mg) | Adhesive strength (N) |
|---|---|---|---|---|---|---|
| 1 | 20 | 40 | 1.0 | 1 | | >330(glass plates broke) |
| 2 | 20 | 40 | 1.0 | 1 | | 100 |
| 3 | — | — | — | — | 10 | 380 |

The invention claimed is:

1. Method for attaching two surfaces to each other consisting of the steps of a) providing a bioadhesive composition consisting of an aqueous solution of a bioadhesive polyphenolic, byssus-forming mussel protein, which protein comprises 30-300 amino acids and consists essentially of tandemly linked peptide repeats comprising 3-15 amino acid residues, wherein at least 3% of the amino acid residues of said bioadhesive polyphenolic protein are L-3.4-dihydroxyphenylalanine (DOPA), wherein the concentration of said bioadhesive polyphenolic protein in said bioadhesive composition is within the range of 10-50 mg/ml;

b) providing a strongly alkaline solution with a pH of 10 or more;

c) (i) mixing said composition and said strongly alkaline solution and applying the mixture to at least one of two surfaces to be attached to each other or (ii) applying said composition and said strongly alkaline solution sequentially, without any specific order, to at least one of two surfaces to be attached to each other, thereby mixing the bioadhesive composition and the strongly alkaline solution;

d) joining said surfaces to each other; and e) leaving said surfaces for sufficiently long time for curing to occur and to produce two surfaces attached to each other, said method being conducted in the absence of an oxidizing agent.

2. Method according to claim 1, wherein the strongly alkaline solution has a pH of 11 or more.

3. Method according to claim 1, wherein at least one of the surfaces to be attached is a biological surface.

4. Method according to claim 1, wherein at least one of the surfaces to be attached is a non-biological surface.

5. The method of claim 1 wherein 6-30% of the amino acid residues of said bioadhesive polyphenolic, byssus-forming mussel protein are DOPA.

6. Method according to claim 5, wherein the strongly alkaline solution has a pH of 11 or more.

7. Method according to claim 5, wherein at least one of the surfaces to be attached is a biological surface.

8. Method according to claim 5, wherein at least one of the surfaces to be attached is a non-biological surface.

9. The method according to claim 1, wherein the strongly alkaline solution has a pH of 11 or more.

10. Method for coating a surface consisting of -the steps of a) providing a bioadhesive composition consisting of an aqueous solution of a bioadhesive polyphenolic, byssus-forming mussel protein, which protein comprises 30-300 amino acids and consists essentially of tandemly linked peptide repeats comprising 3-15 amino acid residues, wherein at least 3% of the amino acid residues of said bioadhesive polyphenolic protein are L-3.4-dihydroxyphenylalanine (DOPA), wherein the concentration of said bioadhesive polyphenolic protein in said bioadhesive composition is within the range of 10-50 mg/ml;

b) providing a strongly alkaline solution with a pH of 10 or more;

c) (i) mixing said composition and said strongly alkaline solution and applying the mixture to the surface to be coated or (ii) applying said composition and said strongly alkaline solution sequentially, without any specific order, to the surface to be coated, thereby mixing the bioadhesive composition and the strongly alkaline solution;

d) leaving said surface for sufficiently long time for curing to occur and to produce a coated surface, said method being conducted in the absence of an oxidizing agent.

11. The method of claim 10 wherein 6-30% of the amino acid residues of said bioadhesive polyphenolic, byssus-forming mussel protein are DOPA.

12. Method according to claim 11, wherein the strongly alkaline solution has a pH of 11 or more.

13. Method according to claim 11, wherein at least one of the surfaces to be attached is a biological surface.

14. Method according to claim 11, wherein at least one of the surfaces to be attached is a non-biological surface.

15. The method according to claim 10, wherein the surface is a biological surface.

16. The method according to claim 10, wherein the surface is a non-biological surface.

* * * * *